US009055968B2

(12) United States Patent
Sekino et al.

(10) Patent No.: US 9,055,968 B2
(45) Date of Patent: *Jun. 16, 2015

(54) LIQUID INJECTION DEVICE

(71) Applicant: SEIKO EPSON CORPORATION, Tokyo (JP)

(72) Inventors: Hirokazu Sekino, Chino (JP); Takeshi Seto, Chofu (JP); Hideki Kojima, Matsumoto (JP); Takahiro Matsuzaki, Shiojiri (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/948,517

(22) Filed: Jul. 23, 2013

(65) Prior Publication Data

US 2013/0304104 A1  Nov. 14, 2013

Related U.S. Application Data

(63) Continuation of application No. 13/050,635, filed on Mar. 17, 2011, now Pat. No. 8,493,222.

(30) Foreign Application Priority Data

Mar. 23, 2010  (JP) .................................. 2010-065849

(51) Int. Cl.
*G08B 21/00*  (2006.01)
*A61B 17/3203*  (2006.01)

(52) U.S. Cl.
CPC .................................. *A61B 17/3203* (2013.01)

(58) Field of Classification Search
USPC ......... 340/618, 686.1, 825.77, 613–614, 603, 340/612, 626, 642, 660, 680, 692
See application file for complete search history.

(56) References Cited

U.S. PATENT DOCUMENTS

| 5,088,467 | A | | 2/1992 | Mesenich |
| 5,836,302 | A | * | 11/1998 | Homuth et al. .......... 128/205.23 |
| 6,140,991 | A | | 10/2000 | Miyabe |
| 7,535,543 | B2 | * | 5/2009 | Dewa et al. .................... 349/161 |
| 7,801,315 | B2 | * | 9/2010 | Watanabe et al. ............... 381/77 |
| 2007/0075610 | A1 | * | 4/2007 | Manabe et al. ............... 310/348 |
| 2007/0250248 | A1 | | 10/2007 | Frank et al. |
| 2008/0086077 | A1 | * | 4/2008 | Seto et al. ........................ 604/48 |
| 2008/0141784 | A1 | * | 6/2008 | Murakami ................. 73/861.18 |
| 2010/0069937 | A1 | | 3/2010 | Seto et al. |

FOREIGN PATENT DOCUMENTS

| JP | 03-166978 | 7/1991 |
| JP | 06-191021 | 7/1994 |

(Continued)

*Primary Examiner* — Daniel Previl (74) *Attorney, Agent, or Firm* — Workman Nydegger (57) ABSTRACT

A liquid injection device includes: a chamber which supply of the liquid and connects with the injection nozzle; a chamber volume varying unit to which driving voltage is applied to reduce the volume of the chamber to a volume smaller than the volume of the chamber before the driving voltage is applied; a driving voltage applying unit which applies the driving voltage to the chamber volume varying unit with the liquid supplied to the chamber; a pseudo noise data memory unit which stores sound data of pseudo noise having audible frequency components contained in driving noise generated when the driving voltage is applied to the chamber volume varying unit; and a pseudo noise outputting unit which outputs the pseudo noise by using the sound data of the pseudo noise such that the sound pressure of the driving noise decreases within the audible frequency range when the driving voltage is applied.

6 Claims, 6 Drawing Sheets

(56) References Cited

FOREIGN PATENT DOCUMENTS

| | | |
|---|---|---|
| JP | 3009118 U | 1/1995 |
| JP | 08-076769 | 3/1996 |
| JP | 2006-076206 | 3/2006 |
| JP | 2007-110535 | 4/2007 |
| JP | 2008-082202 | 4/2008 |

* cited by examiner

| DRIVING VOLTAGE PATTERN SELECTION DIAL | CANCEL SOUND DATA |
|---|---|
| PATTERN A | CANCEL SOUND A |
| PATTERN B | CANCEL SOUND B |
| PATTERN C | CANCEL SOUND C |
| PATTERN D | CANCEL SOUND D |

LIQUID INJECTION DEVICE

This application is a Continuation of application Ser. No. 13/050,635, filed Mar. 17, 2011, and is expressly incorporated herein by reference. The entire disclosure of Japanese Patent Application No: 2010-065849, filed Mar. 23, 2010 is expressly incorporated by reference herein in its entirety.

BACKGROUND

1. Technical Field

The present invention relates to a technology for injecting liquid from an injection nozzle.

2. Related Art

Recently, a method of incising or excising a living tissue by using liquid such as water and a physiological salt water injected from an injection nozzle toward the living tissue at a high pressure has been developed as a surgical method. A liquid injection device employed for this method includes a liquid chamber filled with liquid to be injected from the injection nozzle, and an actuator for varying the volume of the liquid chamber (JP-A-2008-082202). According to this structure, the volume of the liquid chamber decreases in accordance with operation (expansion) of the actuator. As a result, the liquid within the liquid chamber is pressurized and injected as high-pressure liquid from the injection nozzle.

However, when bubbles are contained in the liquid chamber of the liquid injection device thus constructed, these bubbles contract and absorb the pressure applied to the inside of the liquid chamber. In this case, the liquid within the liquid chamber receives only insufficient pressurization, and thus the capability of incising or excising the living tissue lowers. Therefore, when bubbles are mixed or generated in the liquid chamber, the operation needs to be temporarily stopped so as to remove the bubbles within the liquid chamber by discharge through the injection nozzle or by other methods.

Under the normal operation condition of the liquid injection device (without mixture of bubbles into the liquid chamber or other abnormal conditions), driving noise (chiefly constituted by vibration noise emitted from a component for fixing the actuator or other noise) is generated by the effect of the force produced at the time of pressurization of the liquid within the liquid chamber in accordance with the expansion of the actuator. On the other hand, when the abnormal operation condition such as mixture of bubbles into the liquid chamber occurs, the driving noise generated from the liquid injection device tends to decrease (the frequency or amplitude of the driving noise changes).

However, the tendency of the liquid injection device to decrease the driving noise in accordance with the abnormal operation condition such as mixture of bubbles is completely opposite to the general idea that large abnormal noise generates when a device is in some abnormal operation condition. Thus, an operator of the liquid injection device continues using the device without noticing occurrence of the operational abnormality (existence of bubbles within the liquid chamber) in some cases.

SUMMARY

An advantage of some aspects of the invention is to provide a technology capable of solving the problems arising from the related art described above, as a technology allowing an operator to easily recognize occurrence of an abnormal operation condition such as mixture of bubbles into a liquid chamber.

A liquid injection device injecting liquid from an injection nozzle according to an aspect of the invention includes: a liquid chamber which receives supply of the liquid and connects with the injection nozzle; a liquid chamber volume varying unit to which driving voltage is applied to reduce the volume of the liquid chamber to a volume smaller than the volume of the liquid chamber before the driving voltage is applied; a driving voltage applying unit which applies the driving voltage to the liquid chamber volume varying unit with the liquid supplied to the liquid chamber; a pseudo driving noise data memory unit which stores sound data of pseudo driving noise having at least a part of audible frequency components contained in driving noise generated when the driving voltage is applied to the liquid chamber volume varying unit; and a pseudo driving noise outputting unit which outputs the pseudo driving noise by using the sound data of the pseudo driving noise such that the sound pressure of the driving noise decreases within the audible frequency range when the driving voltage is applied.

The liquid injection device according to this aspect of the invention pressurizes the liquid within the liquid chamber and ejects the pressurized liquid from the injection nozzle as pulses by applying driving voltage to the liquid chamber volume varying unit under the condition in which the liquid is supplied to the liquid chamber. In this case, driving noise is generated by effect of the reaction force produced by pressurization of the liquid within the liquid chamber when the driving voltage is applied. The liquid injection device of this aspect of the invention stores sound data of pseudo driving noise having at least a part of the audible frequency components contained in the driving noise, and outputs the pseudo driving noise for reducing the sound pressure of the driving noise in the audible frequency range by using the sound data of the pseudo driving noise when the driving voltage is applied. The phrase "reducing the sound pressure of the driving noise in the audible frequency range" herein refers to a condition in which the driving noise is not required to be completely cancelled but may be only reduced to have a sound volume smaller for the ears of an operator of the liquid injection device than that of the driving noise when the pseudo driving noise is not outputted.

According to this structure, at least a part of the driving noise generated when the driving voltage is applied can be cancelled by the pseudo driving noise outputted when the driving voltage is applied under the condition in which no bubble is contained in the liquid chamber. As a result, the operator of the liquid driving device feels that the driving noise has decreased to be smaller than the driving noise generated when the pseudo driving noise is not outputted. However, when bubbles are mixed into the liquid chamber, these bubbles contract and change the reaction force produced when the liquid within the liquid chamber is pressurized. As a result, the frequency and the sound pressure of the driving noise generated when the driving voltage is applied are changed. In this case, the pseudo driving noise outputted based on the stored sound data does not cancel the changed driving noise, and thus the operator hears both the changed driving noise and the pseudo driving noise. Accordingly, the pseudo driving noise which cancels and reduces the driving noise when no bubble is contained in the liquid chamber becomes noise (alarm) when the driving noise is changed by mixture of bubbles into the liquid chamber. In this condition, the operator feels that the noise coming from the liquid injection device has suddenly increased, and easily recognizes mixture of the bubbles into the liquid chamber.

When the normal condition is restored by discharge of the bubbles mixed into the liquid chamber from the injection nozzle or by other methods, the driving noise and the pseudo driving noise again come to be cancelled by each other. As a result, the operator feels that the noise has decreased, and easily recognizes discharge of bubbles from the inside of the liquid chamber. Since the relationship between the presence or absence of bubbles within the liquid chamber and the increase or decrease of the driving noise felt by the operator becomes an ordinary relationship in which noise increases when an abnormal condition occurs, the operator can intuitively recognize the presence or absence of bubbles. Thus, the liquid injection device can be constantly used in an appropriate condition.

The liquid injection device of the above aspect of the invention may store the sound data of the pseudo driving noise in accordance with the driving voltage applied to the liquid chamber volume varying unit.

The liquid injection device can change the driving voltage applied to the liquid chamber volume varying unit (such as the level of the applied driving voltage, the waveform of the applied driving voltage, and the period of the applied driving voltage) so as to switch the mode of liquid injection from the injection nozzle. The change of the driving voltage applied to the liquid chamber volume varying unit varies the frequency and the sound pressure of the driving noise generated when the driving voltage is applied. Thus, when sound data of the pseudo driving noise suited for reduction of the sound pressure of the driving noise (reduction of the noise) is stored in correspondence with the driving voltage applied to the liquid chamber volume varying unit, appropriate reduction of the driving noise can be achieved by using the pseudo driving noise outputted based on the sound data of the pseudo driving noise corresponding to the applied driving voltage. In this case, the pseudo driving noise heard as noise is felt as larger noise when bubbles are mixed into the liquid chamber. Thus, the operator can further easily recognize mixture of bubbles into the liquid chamber.

The liquid injection device of this aspect of the invention may decrease the sound pressure of the driving noise within the audible frequency range by outputting the pseudo driving noise with delay from the time when the driving voltage is applied.

The driving noise is generated when the driving voltage is applied. When the pseudo driving noise is outputted with delay from the time when the driving voltage is applied, the phase of the pseudo driving noise can be shifted such that at least a part of the driving noise can be cancelled by the pseudo driving noise. As a result, the operator can easily recognize mixture of bubbles into the liquid chamber when bubbles are mixed into the liquid chamber.

The liquid injection device of this aspect of the invention may have an output timing control unit which controls the time when the pseudo driving noise is outputted with delay from the time when the driving voltage is applied.

When the output timing of the pseudo driving noise is controlled such that the driving noise practically generated can be reduced to the minimum, the appropriate output timing can be easily established. Moreover, the driving noise can be appropriately reduced.

The liquid injection device of this aspect of the invention may decreases the sound pressure of the driving noise in the audible frequency range by outputting the pseudo driving noise having the phase opposite to the phase of at least a part of the audible frequency components of the driving noise in accordance with the time when the driving voltage is applied.

As explained above, the driving noise is generated when the driving voltage is applied. When the pseudo driving noise having the phase opposite to the phase of the driving noise is outputted in accordance with the time when the driving voltage is applied, at least a part of the driving noise can be cancelled by the pseudo driving noise. As a result, reduction of the driving noise can be achieved. In this case, the pseudo driving noise is only required to be outputted in accordance with the time when the driving voltage is applied. Thus, control over the output timing is facilitated.

The liquid injection device of this aspect of the invention may perform the following processes. Initially, the driving noise generated when the driving voltage is applied is obtained by a driving noise obtaining unit. Subsequently, sound data of the pseudo driving noise is produced based on the obtained driving noise, and then stored.

According to this structure, sound data of the pseudo driving noise suited for reduction of the driving noise generated when the driving voltage is applied can be produced based on the practically generated driving noise. In this case, the driving noise can be appropriately cancelled by the pseudo driving noise outputted based on the sound data of the pseudo driving noise for reduction of the driving noise. Accordingly, the operator can easily recognize mixture of bubbles into the liquid chamber when bubbles are mixed into the liquid chamber.

The liquid injection device of this aspect of the invention may store sound data having the sine waveform corresponding to any one frequency of audible frequency components contained in the driving noise as sound data of the pseudo driving noise.

The driving noise practically generated when the driving voltage is applied contains various frequency components. Thus, reduction of the driving noise can be easily achieved by outputting the pseudo driving noise based on sound data having the sine waveform corresponding to any one frequency of the audible frequency components contained in the driving noise as the sound data of the pseudo driving noise. Particularly, when the pseudo driving noise is outputted based on the sound data having the sine waveform corresponding to the frequency of the components having the highest sound pressure in the driving noise, a high noise reduction effect can be produced.

The liquid injection device of this aspect of the invention may perform the following processes. Initially, a sine wave control unit which controls at least either the phase of the sine waveform or the amplitude of the sine waveform is provided. The pseudo driving noise is outputted by using sound data of the pseudo driving noise obtained after control of at least either the phase or the amplitude of the sine waveform.

When the phase or the amplitude of the sine waveform is controllable in accordance with the actual driving noise as in this structure, the waveform of the pseudo driving noise to be outputted can be made similar to the waveform of the driving noise. Thus, reduction of the driving noise can be achieved with high accuracy.

BRIEF DESCRIPTION OF THE DRAWINGS

The invention will be described with reference to the accompanying drawings, wherein like numbers reference like elements.

DESCRIPTION OF EXEMPLARY EMBODIMENT

An embodiment according to the invention is hereinafter described in the following order for clarifying the details of the invention.
A. Device Structure:
  A-1. Structure of Liquid Injection Device:
  A-2. Structure of Injection Mechanism:
B. Cancel Sound Output Operation in This Embodiment:
C. Modified example:
  C-1. First Modified Example:
  C-2. Second Modified Example:

A. Device Structure

A-1. Structure of Liquid Injection Device

Figure 1:
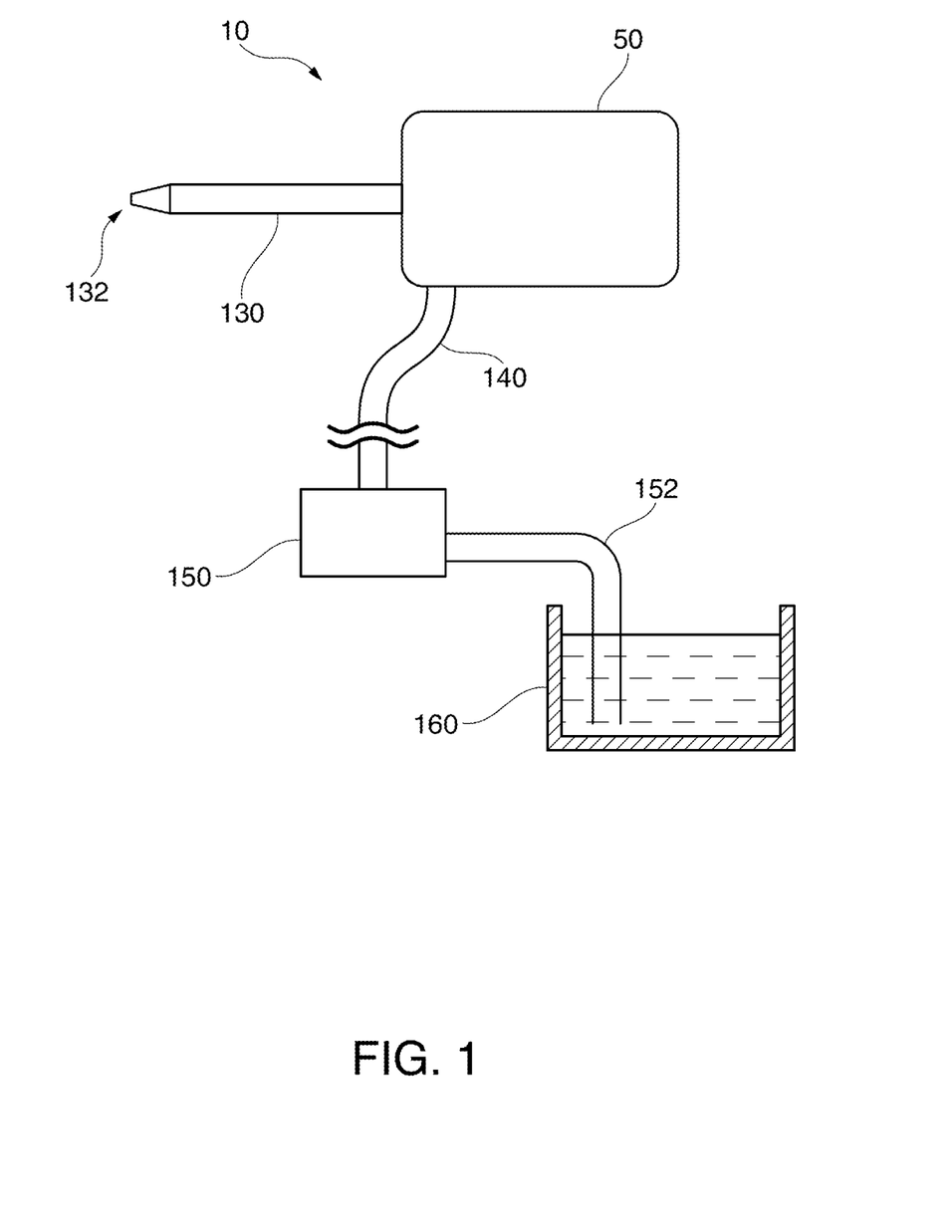
FIG. 1 illustrates the general structure of a liquid injection device according to an embodiment.

FIG. 1 illustrates the general structure of a liquid injection device 10 according to this embodiment. The liquid injection device 10 shown in the figure is employed for performing an operation which incises or excises a living tissue by injecting liquid such as water and physiological salt water toward the living tissue at a high pressure. However, the liquid injection device 10 may be used for other purposes.

As illustrated in the figure, the liquid injection device 10 in this embodiment includes an injection mechanism 50 for pressurizing liquid such as water and physiological salt water and injecting the pressurized liquid, a supply pump 150 for supplying liquid to be injected toward the injection mechanism 50, a liquid tank 160 for containing liquid to be injected, and others. The supply pump 150 is connected with the liquid tank 160 via a liquid channel 152. Liquid sucked from the liquid tank 160 by using the supply pump 150 is supplied to the injection mechanism 50 via a connection tube 140.

A channel tube 130 having an injection port 132 (injection nozzle) at the top end is connected with the injection mechanism 50 such that liquid pressurized within the injection mechanism 50 can be conveyed through the channel tube 130 and injected from the injection port 132 at the top end. For incising or excising a living tissue, an operator of the liquid injection device 10 holds a case 100 of the injection mechanism 50 and ejects liquid while pointing the injection port 132 at the living tissue as the incision or excision target.

A-2. Structure of Injection Mechanism

Figure 2A:
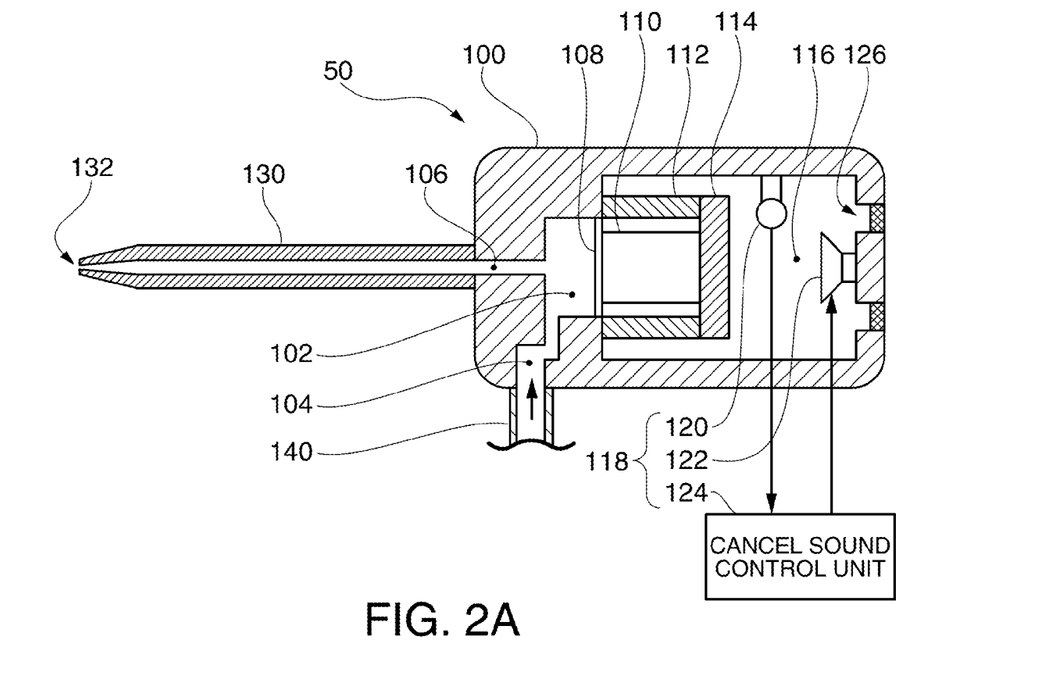
FIGS. 2A and 2B are cross-sectional views illustrating the structure of an injection mechanism mounted on the liquid injection device according to the embodiment.
Figure 2B:
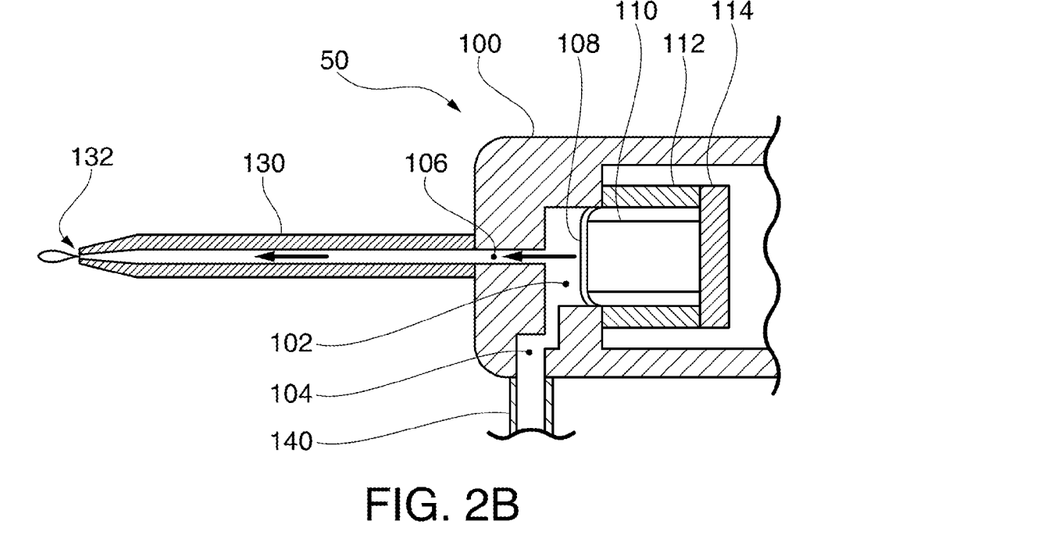

FIGS. 2A and 2B are cross-sectional views illustrating the structure of the injection mechanism 50 mounted on the liquid injection device 10 according to this embodiment. As illustrated in FIG. 2A, the injection mechanism 50 includes a liquid chamber 102 filled with liquid such as water and physiological salt water, a supply channel 104 for guiding liquid supplied by the supply pump 150 toward the liquid chamber 102, an injection channel 106 for guiding liquid within the liquid chamber 102 toward the channel tube 130, and others, and all of these components are accommodated within a case 100 made of lightweight material having a certain strength such as plastics. One end surface of the liquid chamber 102 corresponds to a diaphragm 108 formed by a thin metal plate or the like.

A piezoelectric device 110 as an actuator for varying the volume of the liquid chamber 102 is provided within the case 100 of the injection mechanism 50. The piezoelectric device 110 is fixed to a plate-shaped member 114 called a bottom plate. Under the condition in which the piezoelectric device 110 is accommodated within a cylindrical housing 112 to which the plate-shaped member 114 is fixed, the piezoelectric device 110 comes into contact with the surface of the diaphragm 108 on the side opposite to the liquid chamber 102 such that the piezoelectric device 110 and the diaphragm 108 can be bonded to each other. The piezoelectric device 110 thus disposed expands when driving voltage is applied thereto. This expansion of the piezoelectric device 110 allows injection of liquid in the following manner.

Initially, when driving voltage is not applied to the piezoelectric device 110, the piezoelectric device 110 does not expand as illustrated in FIG. 2A. In this condition, the liquid chamber 102 is filled with liquid such as water and physiological salt water supplied from the supply pump 150. When driving voltage is applied to the piezoelectric device 110 from a not-shown power source (driving voltage applying unit) with the liquid chamber 102 filled with liquid, the piezoelectric device 110 expands and pushes the diaphragm 108 toward the liquid chamber 102 as illustrated in FIG. 2B. As a result, the volume of the liquid chamber 102 decreases, thereby pressurizing the liquid within the liquid chamber 102. As explained above, the two channels of the supply channel 104 and the injection channel 106 are connected with the liquid chamber 102. However, since these channels 104 and 106 are narrow, the liquid contained in the liquid chamber 102 can be sufficiently pressurized by reduction of the volume of the liquid chamber 102 in accordance with the expansion of the piezoelectric device 110. Accordingly, the piezoelectric device 110 and the diaphragm 108 constitute a liquid chamber volume varying unit for reducing the volume of the liquid chamber 102.

The pressurized liquid within the liquid chamber 102 is pushed out toward the injection channel 106 connected with the liquid chamber 102. In this case, the liquid within the liquid chamber 102 is pushed not only toward the injection channel 106 but also toward the supply channel 104. However, since the easiness of introduction of liquid into a channel is determined by the length, the cross-sectional area and the like of the channel, the flow amount of liquid into the supply channel 104 can be made smaller than the flow amount of liquid into the injection channel 106 by setting the lengths and the cross-sectional areas of the supply channel 104 and the injection channel 106 in an appropriate manner. By this method, most of the pressurized liquid within the liquid chamber 102 is pushed toward the injection channel 106, and then conveyed through the channel tube 130 and injected from the injection port 132 at the top end at a high flow speed. According to the liquid injection device 10 in this embodiment, the inside diameter of the injection port 132 is made smaller than the inside diameter of the channel tube 130.

Thus, the flow speed of the liquid injected from the injection port 132 can be further increased.

After the liquid is injected in the manner described above, the driving voltage applied to the piezoelectric device 110 is stopped (the driving voltage is reduced) to return the length of the piezoelectric device 110 to the original length. As a result, the volume of the liquid chamber 102 is returned to the original volume, allowing liquid to be supplied from the supply pump 150 to the liquid chamber 102 (see FIG. 2A). When the piezoelectric device 110 is again expanded by applying the driving voltage thereto (see FIG. 2B), liquid can be again injected from the injection port 132 at a high flow speed. Accordingly, the liquid injection device 10 in this embodiment achieves injection of liquid having a high flow speed as pulses by repeating these processes, and increases the capability of incising or excising a living tissue by utilizing a high pressure produced when the liquid injected at the high flow speed collides with the living tissue.

When the piezoelectric device 110 is actuated for injection of liquid, driving noise uncomfortable for the ears of the operator of the liquid injection device 10 is produced from the inside of the injection mechanism 50. This driving noise is generated by the contraction and expansion of the piezoelectric device 110, or vibration of components such as the plate-shaped member 114 and the housing 112 for fixing the piezoelectric device 110 caused by the reaction force produced when the piezoelectric device 110 pressurizes the liquid within the liquid chamber 102.

Therefore, the liquid injection device 10 in this embodiment includes a noise reducing mechanism 118 for reducing driving noise (decreasing sound pressure of driving noise) generated by injection of liquid. As illustrated in FIG. 2A, the noise reducing mechanism 118 includes a microphone 120 (driving noise obtaining unit) which samples driving noise generated from the injection mechanism 50, a speaker 122 (pseudo driving noise outputting unit) which generates cancel sound (pseudo driving noise) for canceling (counterbalancing) the sampled driving noise, a cancel sound control unit 124 which controls the cancel sound generated based on the sampled driving noise, and others. According to this embodiment, a space 116 is provided around the housing 112 and the plate-shaped member 114 within the case 100 of the injection mechanism 50 as a space for accommodating the microphone 120 and the speaker 122. The speaker 122 is disposed in such a position as to face the plate-shaped member 114 as the chief source for generating the driving noise. According to this embodiment, the cancel sound control unit 124 is provided separately from the case 100 of the injection mechanism 50. However, when the case 100 of the injection mechanism 50 has a sufficient space, the cancel sound control unit 124 may be disposed within the case 100.

Figure 3:
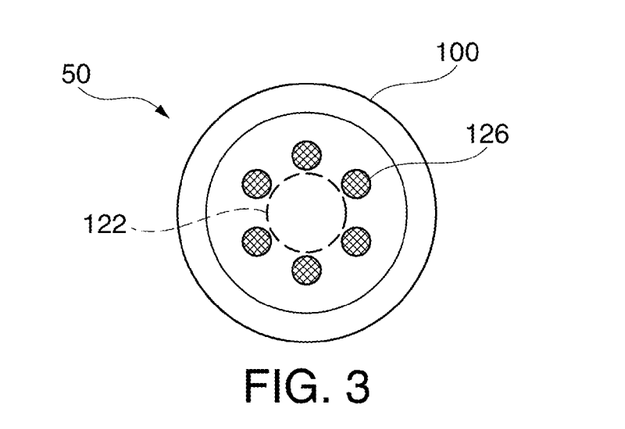
FIG. 3 illustrates through holes formed on a case of the injection mechanism.

The case 100 of the injection mechanism 50 has through holes 126 penetrated to connect the inside space 116 and the outside. According to this embodiment, the six through holes 126 are formed on the end surface of the case 100 to which the speaker 122 is attached in such positions as to surround the speaker 122 as illustrated in FIG. 3. When an abnormal operation condition such as mixture of bubbles into the liquid chamber 102 of the injection mechanism. 50 occurs in the liquid injection device 10 in this embodiment, cancel sound outputted from the speaker 120 leaks through the through holes 126 to be heard, allowing the operator of the liquid injection device 10 to easily recognize occurrence of the abnormal operation condition. This point will be described in detail later. A mesh engages with each of the through holes 126 to prevent entrance of contaminants into the case 100.

The liquid injection device 10 in this embodiment ejects liquid having a high flow speed from the injection port 132 as pulses, and also reduces driving noise generated at the time of injection of liquid by using the injection mechanism 50 thus constructed. The operation performed when the liquid injection device 10 in this embodiment outputs cancel sound used for reducing driving noise generated by injection of liquid is now explained.

B. Cancel Sound Output Operation in this Embodiment

Figure 4:
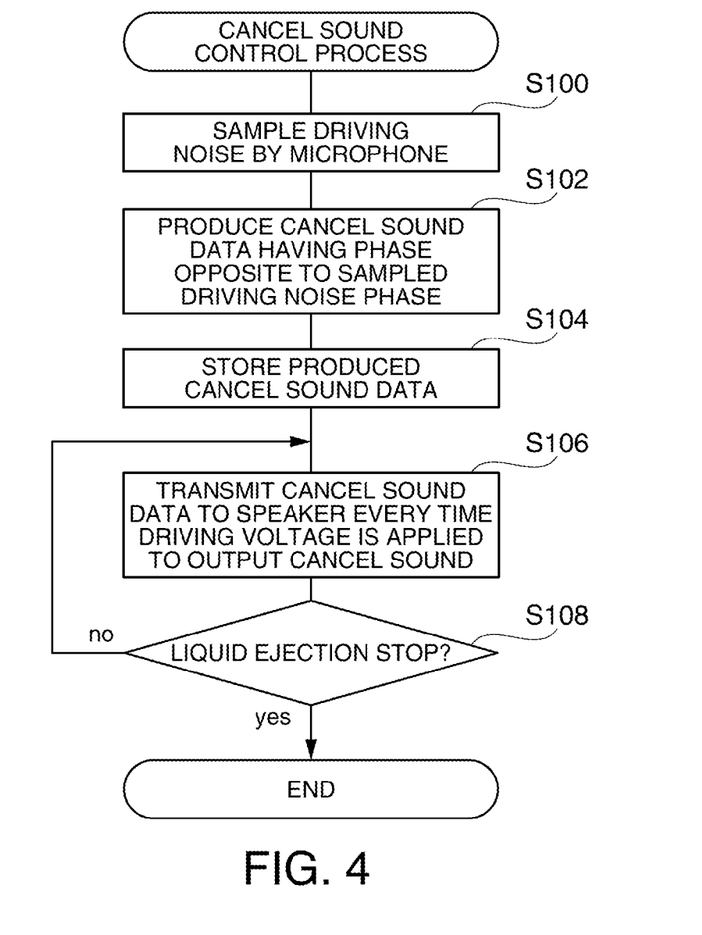
FIG. 4 is a flowchart showing the flow of a process performed by the liquid injection device according to the embodiment for outputting cancel sound (cancel sound control process).

FIG. 4 is a flowchart showing the flow of the process performed when the liquid injection device 10 in this embodiment outputs cancel sound (cancel sound control process). This process is executed by the cancel sound control unit 124 (corresponding to a pseudo driving noise data producing unit) in response to the start of liquid injection.

When the cancel sound control process is initiated, the microphone 120 provided within the case 100 samples driving noise generated within the case 100 of the injection mechanism 50 by injection of liquid (step S100). As explained above, the liquid injection device 10 in this embodiment applies driving voltage to the piezoelectric device 110 to eject liquid as pulses. Since the driving noise is produced by expansion of the piezoelectric device 110 caused when the driving voltage is applied thereto, in step S100 the driving noise is sampled in such cycles each of which continues from the time when the driving voltage is applied until the time when the driving voltage is applied next.

After the driving noise is sampled, the phase of the sampled driving noise is reversed to produce cancel sound data having the opposite phase (sound data of pseudo driving noise) (step S102). Then, the produced cancel sound data is stored (step S104). The frequency of the driving noise is dependent on the frequency of the driving voltage applied to the piezoelectric device 110 (driving frequency), and the frequencies of the intensive components of the driving noise are contained in the frequency bands corresponding to the driving frequencies multiplied by integers. This point will be described in detail later. According to the liquid injection device 10 in this embodiment, a cancel sound data memory unit (pseudo driving noise data memory unit) is included in the cancel sound control unit 124, and the produced cancel sound data is stored in the cancel sound data memory unit.

After the cancel sound data having the phase opposite to the phase of the driving noise is stored, the cancel sound data is transmitted to the speaker 122 at the time when the driving voltage is applied to the piezoelectric device 110. Then, the cancel sound is outputted from the speaker 122 based on the transmitted data (step S106). As explained above, the speaker 122 is disposed in such a position as to face the plate-shaped member 114 as the chief source for generating the driving noise (see FIG. 2A). Thus, emission of the driving noise uncomfortable for the operator of the liquid injection device 10 can be reduced (the sound pressure of the driving noise can be decreased) by mutual cancellation between the driving noise and the cancel sound from the speaker 122.

After the cancel sound is outputted from the speaker 122 based on the cancel sound data transmitted thereto, it is determined whether injection of liquid is stopped or not (step S108). While injection of liquid is being stopped, that is, the piezoelectric device 110 is not being actuated, the driving noise is not produced. In this case, the cancel sound need not be outputted. Thus, whether injection of liquid is stopped or not is checked in the step S108.

While injection of liquid is being continued (step S108: NO), the flow returns to the step S106 to reduce the driving noise generated by injection of liquid. In this case, the cancel sound data is transmitted to the speaker 122 at the time when the driving voltage is applied to the piezoelectric device 110, and the cancel sound is outputted from the speaker 122. When injection of liquid is stopped after repetitions of the process of outputting the cancel sound from the speaker 122 every time the driving voltage is applied to the piezoelectric device 110 (step S108: YES), the cancel sound control process shown in FIG. 4 ends.

The liquid injection device 10 in this embodiment outputs the cancel sound having the phase opposite to the phase of the driving noise from the speaker 122 by executing the cancel sound control process explained above for reduction of the driving noise generated at the time of injection of liquid. As mentioned above, the liquid injection device 10 in this embodiment stores the cancel sound data produced based on the driving noise sampled by the microphone 120, and outputs the cancel sound by using the stored cancel sound data. Since the driving noise is reduced by the output of the fixed cancel sound, the cancel sound functions as alarm when an abnormal operation condition such as mixture of bubbles into the liquid chamber 102 occurs. Thus, the operator of the liquid injection device 10 can easily recognize occurrence of the abnormal operation condition. This point is now explained in detail.

Figure 5A:
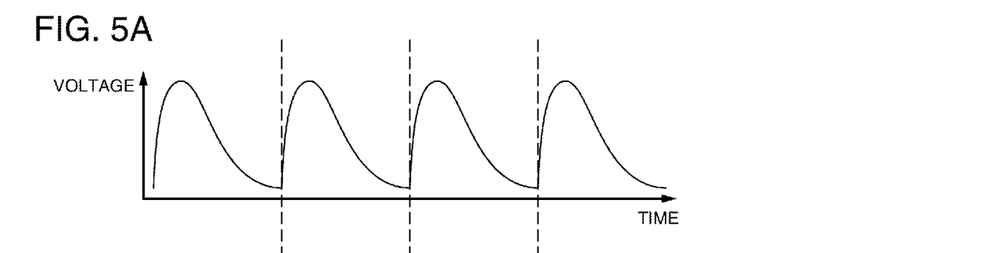
FIGS. 5A through 5D show a condition in which cancel sound functions as alarm when an abnormal operation condition such as mixture of bubbles into a liquid chamber of the injection mechanism occurs.

FIGS. 5A through 5D illustrate a condition in which the cancel sound functions as alarm when an abnormal operation condition such as mixture of bubbles into the liquid chamber 102 of the injection mechanism 50 occurs. FIG. 5A shows driving voltage applied to the piezoelectric device 110 for injection of liquid as an example condition. As explained above, when the driving voltage is applied to the piezoelectric device 110, the piezoelectric device 110 expands and decreases the volume of the liquid chamber 102. As a result, the pressurized liquid within the liquid chamber 102 is injected from the injection port 132. When the driving voltage applied to the piezoelectric device 110 is lowered after the liquid injection, the length of the piezoelectric device 110 returns to the original length. Consequently, the volume of the liquid chamber 102 returns to the original volume, allowing the liquid chamber 102 to be filled with liquid. Then, the driving voltage is again applied to the piezoelectric device 110 to eject high-pressure liquid from the injection port 132. Accordingly, the driving voltage applied to the piezoelectric device 110 in this manner achieves injection of liquid as pulses.

Figure 5B:
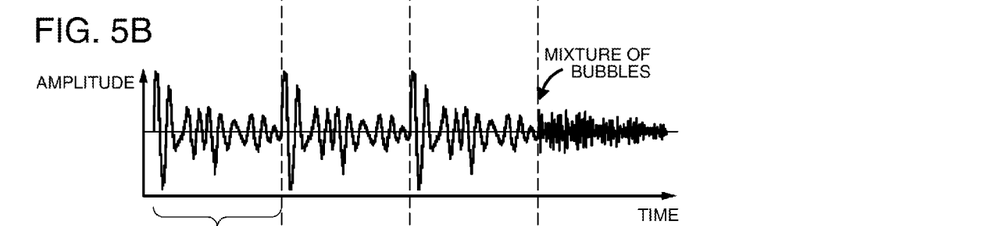

With injection of liquid as pulses, driving noise is generated within the case 100 of the injection mechanism 50. FIG. 5B shows a waveform of the driving noise generated by injection of liquid as an example waveform. This driving noise is chiefly produced by vibration of the plate-shaped member 114, the housing 112 and the like for fixing the piezoelectric device 110 as vibration caused by the reaction force generated when the liquid within the liquid chamber 102 is pressurized by the press of the diaphragm 108 in accordance with the expansion of the piezoelectric device 110. Thus, the amplitude (sound pressure) of the driving noise has a tendency to increase in synchronization with the time when the driving voltage is applied to the piezoelectric device 110, and attenuate when the driving voltage is lowered. The frequency of the driving noise is dependent on the frequency of the driving voltage applied to the piezoelectric device 110 (driving frequency), and the frequencies of the intensive components of the driving noise are contained in the frequency bands corresponding to the driving frequencies multiplied by integers. In case of the driving noise shown in FIG. 5B as an example, the components of the driving noise having the frequency ten times higher than the driving frequency (3 kHz when driving frequency is 300 Hz, for example) exhibit the maximum sound pressure, constituting the main components of the driving noise.

Figure 5C:
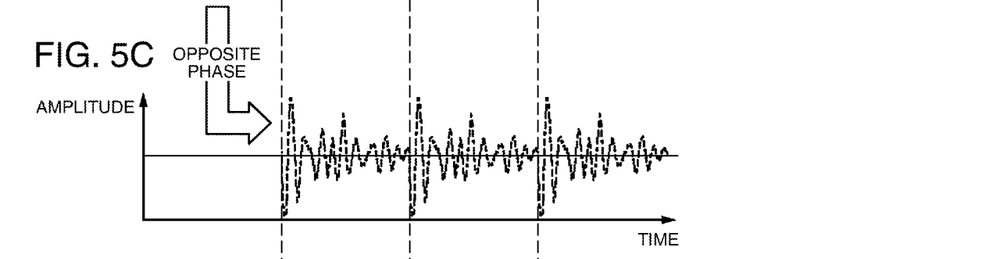

The liquid injection device 10 in this embodiment outputs cancel sound from the speaker 122 in response to the generated driving noise to reduce the driving noise. FIG. 5C shows a waveform of the cancel sound outputted from the speaker 122 as an example. As explained above, the cancel sound data transmitted to the speaker 122 is produced by reversing the phase of the driving noise sampled by the microphone 120 in such cycles each of which continues from the time when the driving voltage is applied to the piezoelectric device 110 until the time when the driving voltage is applied next. Thus, the frequency and amplitude of the cancel sound are the same as those of the driving noise, and only the phase is reversed. The produced cancel sound data is stored, and the stored cancel sound data is transmitted to the speaker 122 every time the driving voltage is applied to the piezoelectric device 110 for output of the cancel sound.

Figure 5D:
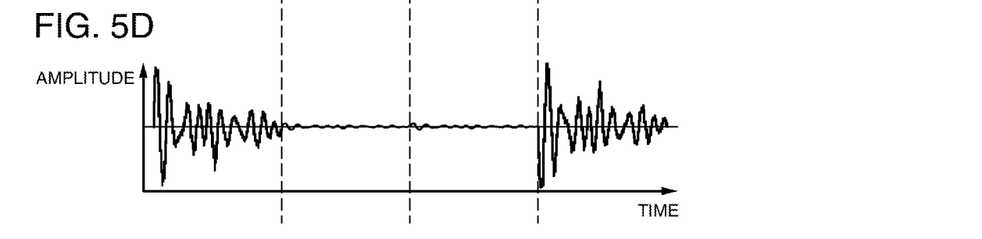

FIG. 5D illustrates the waveform of the driving noise shown in FIG. 5B and the waveform of the cancel sound shown in FIG. 5C as the superimposed waveforms. The operator of the liquid injection device 10 hears sound having the waveforms thus superimposed. When the cancel sound is not outputted from the speaker 122, the driving noise is released as it is and heard by the operator. However, when the cancel sound having the phase opposite to the phase of the driving noise is outputted from the speaker 122, the driving noise is reduced by cancellation between the driving noise and the cancel sound. As a result, the operator hears little noise from the injection mechanism 50. When the driving voltage is applied to the piezoelectric device 110 in fixed patterns with no bubble contained within the liquid chamber 102, the driving noise thus produced becomes substantially constant. Thus, the driving noise can be reduced (the sound pressure of the driving noise can be decreased) even by output of the cancel sound produced based on the stored cancel sound data as in this embodiment.

When bubbles are mixed or generated within the liquid chamber 102, the driving noise varies as shown in FIG. 5B. This phenomenon happens for the following reason. Initially, as explained above, the driving noise is chiefly produced by vibration of the plate-shaped member 114, the housing 112 and the like by the effect of the reaction force generated when the piezoelectric device 110 pressurizes the liquid within the liquid chamber 102. However, when bubbles are contained in the liquid chamber 102, these bubbles contract and absorb the pressure at the time of pressurization of the liquid within the liquid chamber 102 by the piezoelectric device 110. As a result, the reaction force decreases, and the frequency and amplitude (sound pressure) of the driving noise change. In case of the example shown in FIG. 5B, the sound pressure of the main components of the driving noise having the associated frequency (the frequency ten times higher than the driving frequency) when no bubble is contained in the liquid chamber 102 (during normal operation) considerably decreases. In this case, the liquid within the liquid chamber 102 is not sufficiently pressurized due to the presence of the bubbles, and the force of the liquid injected from the injection port 132 lowers. As a result, the capability of incising or excising a living tissue deteriorates. Accordingly, when bubbles are mixed or generated within the liquid chamber 102, the operator of the liquid injection device 10 is required to temporarily stop the operation to remove the bubbles by discharge from the injection port 132 or by other methods. In addition, the tendency that the driving noise generated by the actuation of the piezoelectric device 110 decreases is also recognized when the liquid within the liquid chamber 102 is not appropriately pressurized by the piezoelectric device 110 due to breakage of the diaphragm 108 as well as at the time when bubbles are contained in the liquid chamber 102. In case of the breakage of the diaphragm 108, suspension of the use of the liquid injection device 10 is required.

The liquid injection device 10 in this embodiment outputs the cancel sound by using the stored cancel sound data without change even when the driving noise varies by the mixture of the bubbles into the liquid chamber 102 or for other reasons. Therefore, as shown in FIG. 5C, the cancel sound outputted from the speaker 122 does not change before and after the mixture of the bubbles. In this case, the frequencies and amplitudes of the driving noise varied by the mixture of the bubbles or the like and the cancel sound outputted from the speaker 122 do not agree with each other, and therefore cancellation between the driving noise and the cancel sound becomes difficult.

According to the example shown in FIG. 5D, the cancel sound outputted from the speaker 122 remains without cancellation due to the decrease in the sound pressure of the driving noise caused by the mixture of the bubbles into the liquid chamber 102. As explained above, the case 100 of the injection mechanism 50 in this embodiment has the through holes 126 (see FIG. 3). Thus, when the abnormal operation condition such as mixture of bubbles into the liquid chamber 102 occurs, the cancel sound not cancelled leaks through the through holes 126 to be heard. Accordingly, since the cancel sound decreased by the cancellation with the driving noise during the normal operation of the liquid injection device 10 is heard by the operator of the liquid injection device 10 as noise (alarm) at the time of occurrence of the abnormal operation condition, the operator can easily recognize the operation abnormality. There is a case in which only the frequency of the driving noise varies due to mixture of bubbles into the liquid chamber 102 or for other reasons with the amplitude (sound pressure) of the driving noise kept unchanged unlike the example shown in FIG. 5B. In this case, the driving noise and the cancel sound do not have the opposite-phase relationship but are multiplied by each other. As a result, still larger abnormal noise is heard.

As described above, the liquid injection device 10 in this embodiment stores cancel sound data having the phase opposite to the phase of the driving noise generated by injection of liquid as data produced based on the sampled driving noise, and outputs cancel sound from the speaker 122 based on the stored cancel sound data every time the driving voltage is applied to the piezoelectric device 110 for reduction of the driving noise. Thus, when the driving noise varies at the time of occurrence of an abnormal operation condition such as mixture of bubbles into the liquid chamber 102 of the injection mechanism 50, the driving noise cannot be canceled by the cancel sound but is heard by the operator. Moreover, the cancel sound itself is heard by the operator. As a result, the operator of the liquid injection device 10 feels that noise (alarm) not heard by him or her before suddenly starts to be generated from the injection mechanism 50, and therefore easily recognizes occurrence of operation abnormality.

The liquid injection device 10 in this embodiment samples actually generated driving noise in each cycle continuing from the time when the driving voltage is applied to the piezoelectric device 110 until the time when the driving voltage is applied next by using the built-in microphone 120, and reverses the sampled driving noise to produce cancel sound data. In this case, the cancel sound outputted from the speaker 122 obtains the same frequency and amplitude as those of the driving noise, and the opposite-phase relationship with the driving noise only by transmission of the cancel sound data to the speaker 122 at the time when the driving voltage is applied to the piezoelectric device 110 (in synchronization with the time when the driving voltage is applied). Thus, the driving noise during the normal operation can be appropriately cancelled by the cancel sound and reduced with high accuracy. Accordingly, when an abnormal operation condition such as mixture of bubbles into the liquid chamber 102 occurs, the operator easily recognizes the cancel sound heard as noise which functions as further secure notification about the operational abnormality.

When the operation is restored after discharge of the bubbles mixed in the liquid chamber 102 from the injection port 132, the driving noise and the cancel sound come to be cancelled by each other again in such a condition that emission of the driving noise can be sufficiently prevented. Thus, the operator can easily recognize that the normal condition of the liquid injection device 10 is restored.

C. Modified Example

A first modified example and a second modified example are hereinafter described. In the explanation of the first modified example and the second modified example, similar reference numbers are given to parts similar to the corresponding parts in the embodiment described above, and the same detailed explanation is not repeated.

C-1. First Modified Example

According to the embodiment described above, the cancel sound data is produced based on driving noise sampled by the microphone 120 contained in the injection mechanism 50. However, considering the fact that the driving noise generated by the actuation of the piezoelectric device 110 during the normal operation is substantially constant for each pattern of the driving voltage applied to the piezoelectric device 110, such a structure which stores the cancel sound data beforehand in accordance with the patterns of the driving voltage applied to the piezoelectric device 110 is allowed. The first modified example explained herein employs this structure.

Figure 6:
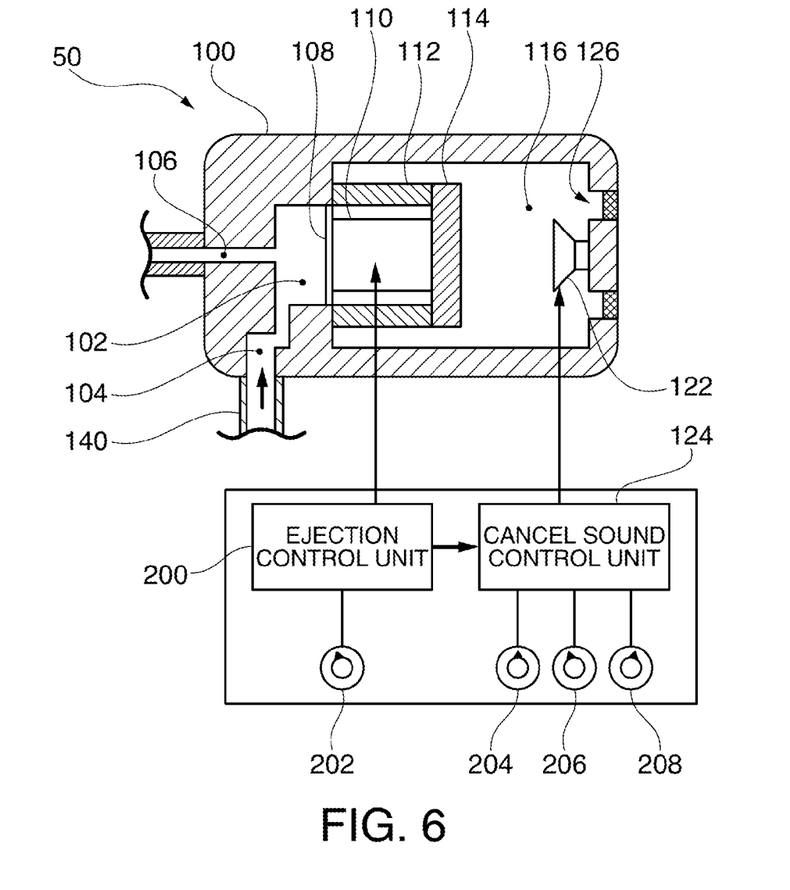
FIG. 6 illustrates the structure of an injection mechanism mounted on a liquid injection device according to a first modified example.

FIG. 6 illustrates the structure of the injection mechanism 50 mounted on the liquid injection device 10 according to the first modified example. Unlike the embodiment described above (see FIGS. 2A and 2B), the liquid injection device 10 in the first modified example does not have the microphone 120 for sampling driving noise. This is because the liquid injection device 10 in the first modified example stores cancel sound data beforehand in correspondence with the patterns of the driving voltage applied to the piezoelectric device 110 (driving voltage patterns) such that the necessity of sampling the driving noise for producing the cancel sound data as in the above embodiment can be eliminated.

According to the liquid injection device 10 in the first modified example which sets a plurality of driving voltage patterns beforehand, a driving voltage pattern selection dial 202 may be connected with an injection control unit 200 which controls the operation for applying the driving voltage to the piezoelectric device 110. The operator of the liquid injection device 10 can select any of the plural driving voltage patterns by switching the driving voltage pattern selection dial 202. The respective driving voltage patterns have different frequencies of the applied driving voltage (driving frequencies) and different levels of the applied driving voltage such that the operator can vary the injection cycle for injecting liquid from the injection port 132 as pulses and the level of the pressure of the liquid to be injected by switching the driving voltage patterns.

When the operator of the liquid injection device 10 selects any of the driving voltage patterns by using the driving voltage pattern selection dial 202 and starts injection of liquid, the injection control unit 200 applies the driving voltage to the piezoelectric device 110 in correspondence with the driving voltage pattern selected by the driving voltage pattern selection dial 202 to actuate the piezoelectric device 110. The injection control unit 200 is connected with the cancel sound control unit 124 which controls cancel sound outputted from the speaker 122 to notify the cancel sound control unit 124 of the selection of the driving voltage pattern prior to the actuation of the piezoelectric device 110.

Figure 7:
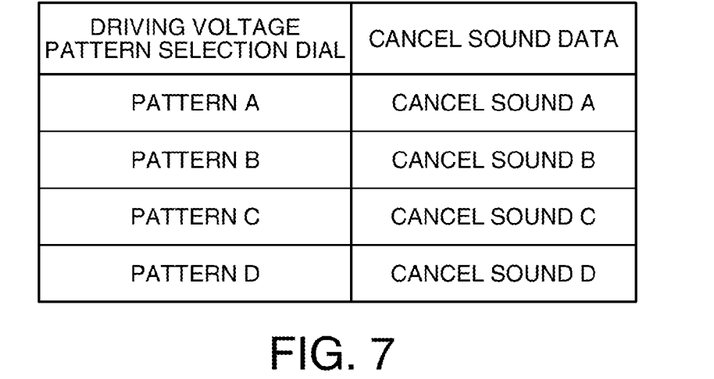
FIG. 7 shows a concept of cancel sound data stored beforehand for each of plural established driving voltage patterns with correlations between the cancel sound data and the driving voltage patterns.

As explained above, the driving noise generated by the actuation of the piezoelectric device 110 changes in accordance with the different selections of the driving voltage pattern. Thus, as shown in FIG. 7, the cancel sound data memory unit contained in the cancel sound control unit 124 stores individual cancel sound data in correspondence with the respective driving voltage patterns with correlations between the cancel sound data and the driving voltage patterns in advance. These cancel sound data are established as data for appropriately reducing driving noise generated when the driving voltage is applied to the piezoelectric device 110 in accordance with the corresponding driving voltage pattern under the condition in which no bubble is contained in the liquid chamber 102 (normal operation condition) (that is, data having the phase opposite to the phase of the driving noise), and stored in such cycles each of which continues from the time when the driving voltage is applied until the time when the driving voltage is applied next.

The cancel sound control unit 124 reads the cancel sound data corresponding to the driving voltage pattern selected by the driving voltage pattern selection dial 202 while referring to the table shown in FIG. 7, and transmits the cancel sound data to the speaker 122 at the time when the driving voltage is applied to the piezoelectric device 110 to output the cancel sound.

As illustrated in FIG. 6, in case of the liquid injection device 10 in the first modified example, a frequency control dial 204 for controlling the frequency of the cancel sound data, an amplitude control dial 206 for controlling the amplitude of the cancel sound data, and a phase control dial 208 for controlling the phase of the cancel sound data may be connected with the cancel sound control unit 124. Moreover, fine control of the timing for transmitting the cancel sound data may be performed by using a not-shown output timing control unit according to the setting of the phase control dial 208. The driving noise generated by the actuation of the piezoelectric device 110 slightly varies in accordance with the different types of the liquid to be injected (that is, liquid supplied to the liquid chamber 102) or the like in some cases. However, the operator of the liquid injection device 10 can establish the condition for reducing the driving noise to the minimum by operating these dials.

Accordingly, the liquid injection device 10 in the first modified example can reduce the driving noise generated at the time of actuation of the piezoelectric device 110 by the cancellation between the driving noise and the cancel sound outputted from the speaker 122 under the normal operation condition similarly to the embodiment described above. When the driving noise varies by occurrence of an abnormal operation condition such as mixture of bubbles into the liquid chamber 102, the driving noise cannot be cancelled by the cancel sound but is heard by the operator of the liquid injection device 10. Moreover, the cancel sound itself is heard by the operator. Thus, the operator can easily recognize generation of the operational abnormality.

According to the liquid injection device 10 in the first modified example, the cancel sound data is stored beforehand for each pattern of the plural established driving voltage patterns. Thus, the necessity of providing the microphone for sampling the driving noise inside the injection mechanism 50 can be eliminated, which makes the injection mechanism 50 compact. Moreover, the possibility of malfunction that the cancel sound data is produced based on sound obtained by the microphone as sound existing therearound can be eliminated, which stabilizes the condition for noise reduction.

Furthermore, when the frequency control dial 204, the amplitude control dial 206, and the phase control dial 208 are provided, the frequency, the amplitude, and the phase of the cancel sound can be controlled such that the driving noise actually generated can be reduced to the minimum. Thus, the driving noise during the normal operation can be reduced with high accuracy. Accordingly, when an abnormal operation condition such as mixture of bubbles into the liquid chamber 102 occurs, the operator of the liquid injection device 10 feels that the cancel sound heard as noise has increased, and thus can easily recognize generation of the operational abnormality.

C-2. Second Modified Example

According to the embodiment and the first modified example described above, the cancel sound is outputted based on the cancel sound data having the phase opposite to the phase of the driving noise. However, the cancel sound data is not limited to the data having the phase opposite to the phase of the driving noise but may be sine wave cancel sound data for outputting the cancel sound. The second modified example explained herein employs this structure.

Figure 8A:
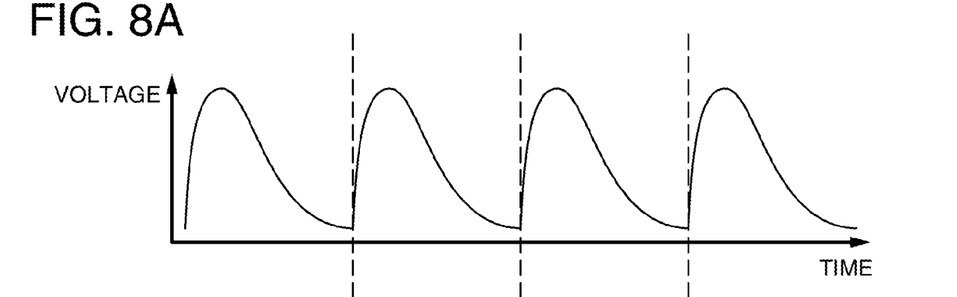
FIGS. 8A through 8D show a condition in which a liquid injection device according to a second modified example reduces driving noise by using cancel sound outputted based on sine wave cancel sound data.
Figure 8B:
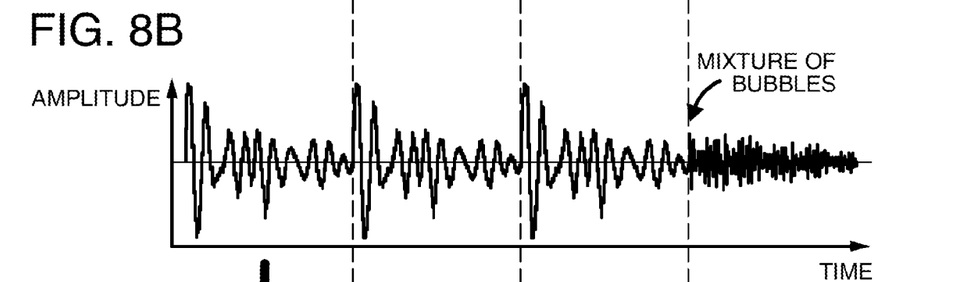

FIGS. 8A through 8D show a condition in which the liquid injection device 10 in the second modified example reduces driving noise by using cancel sound outputted based on sine wave cancel sound data. FIG. 8A shows driving voltage applied to the piezoelectric device 110 to eject liquid as pulses. FIG. 8B shows a waveform of driving noise generated by the actuation of the piezoelectric device 110 as an example.

For reducing this driving noise, the liquid injection device 10 in the second modified example transmits cancel sound data having a sine waveform from the cancel sound control unit 124 to the speaker 122 to output the cancel sound. It is preferable that the sine waveform of the cancel sound data corresponds to the sine waveform at the frequency exhibiting the largest sound pressure in the frequencies of the driving noise. In this case, the effect of noise reduction increases.

Figure 8C:
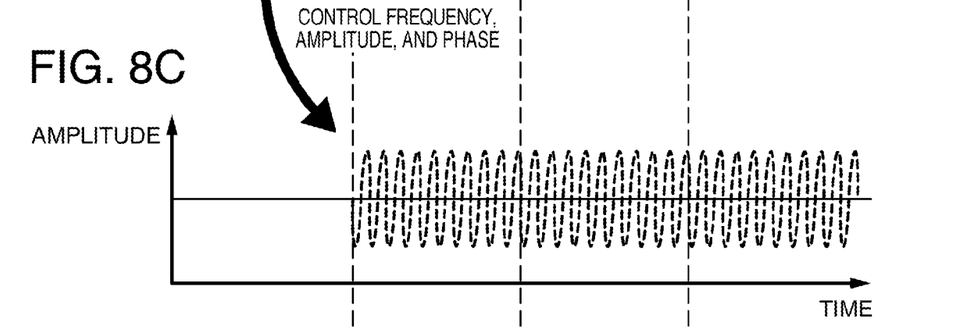

According to the liquid injection device 10 in the second modified example, the frequency control dial 204, the amplitude control dial 206, and the phase control dial 208 (sine wave control unit) may be connected with the cancel sound control unit 124 similarly to the first modified example (see FIG. 6). The operator of the liquid injection device 10 can control the frequency, amplitude, and phase of the cancel sound data to be transmitted to the speaker 122 by using these dials such that the driving noise can be reduced to the minimum. The cancel sound control unit 124 transmits the cancel sound data thus controlled to the speaker 122 every time the driving voltage is applied to the piezoelectric device 110. FIG. 8C shows a waveform of cancel sound outputted from the speaker 122 based on the cancel sound data controlled in accordance with the driving noise as an example. For providing the opposite-phase relationship between the driving noise generated by the actuation of the piezoelectric device 110 and the cancel sound outputted from the speaker 122, the cancel sound data having the same phase as that of the driving noise may be transmitted to the speaker 122 with delay of half cycle from the time when the driving voltage is applied to the piezoelectric device 110. Moreover, fine control of the timing for transmitting the cancel sound data may be performed by using the not-shown output timing control unit in correspondence with the setting of the phase control dial 208.

Figure 8D:
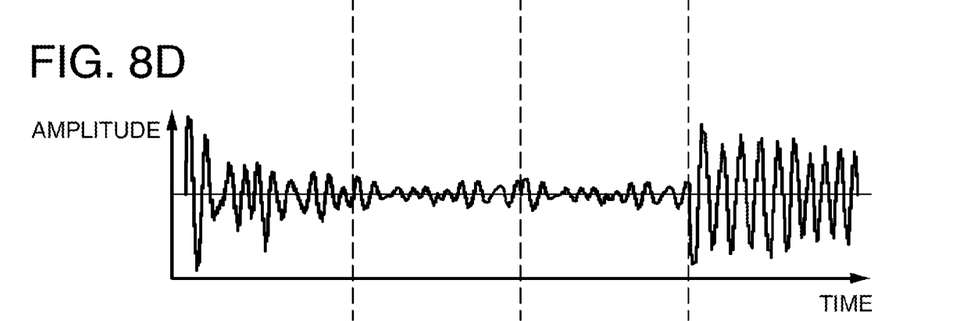

FIG. 8D illustrates the waveform of the driving noise shown in FIG. 8B and the waveform of the cancel sound shown in FIG. 8C as superimposed waveforms. Since the frequencies and amplitudes of the cancel sound outputted from the speaker 122 and the driving noise actually generated do not completely agree with each other, perfect cancellation cannot be achieved. However, the sound pressure of the noise heard by the operator of the liquid injection device 10 can be reduced to be at least lower than when the cancel sound is not outputted at all.

When the driving noise varies at the time of occurrence of an abnormal operation condition such as mixture of bubbles into the liquid chamber 102 after the noise reduction, the cancel sound optimized for the driving noise during the normal operation and the varied driving noise are not cancelled by each other but multiplied by each other. As a result, the operator feels that the noise has increased and thus can easily recognize generation of operational abnormality.

As described above, the liquid injection device 10 in the second modified example may control the frequency, amplitude, and phase of the sine waveform cancel sound data such that the driving noise during the normal operation can be reduced to the minimum for the output of the cancel sound. Considering the fact that the driving noise practically generated when the driving voltage is applied to the piezoelectric device 110 contains various frequency components, output of the cancel sound capable of reducing the sound pressure of the driving noise generated during the normal operation can be easily achieved by controlling the frequency, amplitude, phase of the cancel sound data in accordance with the actual driving noise based on the sine waveform cancel sound data.

According to the example shown in FIG. 8C, the amplitude of the cancel sound approximated by sine waves becomes constant after the control by the amplitude control dial 206. However, since the amplitude of the driving noise practically generated tends to attenuate with decrease in the driving voltage, the amplitude of the cancel sound may be made attenuate accordingly. In this case, when an attenuation factor control dial for controlling the attenuation factor of the amplitude of the cancel sound data is connected with the cancel sound control unit 124, the waveform of the cancel sound can be made similar to the waveform of the driving noise, which further improves the accuracy of noise reduction.

The liquid injection device according to the invention is not limited to the embodiment and respective modified examples described herein but may be practiced otherwise without departing from the scope of the invention.

What is claimed is:

1. A surgical device injecting liquid from an injection nozzle, comprising:
   a liquid chamber which receives supply of the liquid and connects with the injection nozzle;
   a liquid chamber volume varying unit to which driving voltage is applied to reduce the volume of the liquid chamber to a volume smaller than the volume of the liquid chamber before the driving voltage is applied;
   a driving voltage applying unit which applies the driving voltage to the liquid chamber volume varying unit with the liquid supplied to the liquid chamber;
   a pseudo driving sound outputting unit which outputs the pseudo driving sound such that a sound pressure of a driving sound decreases within an audible frequency range when the driving voltage is applied.

2. The surgical device according to claim 1, wherein the pseudo driving sound outputting unit is a unit which decreases the sound pressure of the driving sound within the audible frequency range by outputting the pseudo driving sound with delay from the time when the driving voltage is applied.

3. The surgical device according to claim 2, wherein the pseudo driving sound outputting unit has an output timing control unit which controls the time when the pseudo driving sound is outputted with delay from the time when the driving voltage is applied.

4. A surgical device injecting liquid from an injection nozzle, comprising:
   a liquid chamber which receives supply of the liquid and connects with the injection nozzle;
   a liquid chamber volume varying unit to which driving voltage is applied to reduce the volume of the liquid chamber to a volume smaller than the volume of the liquid chamber before the driving voltage is applied;
   a driving voltage applying unit which applies the driving voltage to the liquid chamber volume varying unit with the liquid supplied to the liquid chamber;
   a pseudo sound outputting unit which outputs a pseudo driving sound.

5. The surgical device according to claim 4, wherein the pseudo sound outputting unit is a unit which decreases the sound pressure of the driving sound within the audible frequency range.

6. The surgical device according to claim 5, wherein the pseudo sound outputting unit has an output timing control unit which controls the time when the pseudo sound is outputted with delay from the time when the driving voltage is applied.

* * * * *